United States Patent [19]

Hooven et al.

[11] Patent Number: 4,627,832

[45] Date of Patent: Dec. 9, 1986

[54] THREE STAGE INTRACRANIAL PRESSURE RELIEF VALVE HAVING SINGLE-PIECE VALVE STEM

[75] Inventors: Michael D. Hooven, Miami, Fla.; Christian Sainte-Rose, Paris, France

[73] Assignee: Cordis Corporation, Miami, Fla.

[21] Appl. No.: 608,137

[22] Filed: May 8, 1984

[51] Int. Cl.$^4$ ............................................. A61M 5/00
[52] U.S. Cl. ....................................... 604/9; 604/247; 604/249; 137/508
[58] Field of Search ........................................ 604/8-10, 604/247, 249; 137/508, 510

[56] References Cited

U.S. PATENT DOCUMENTS

| | | | |
|---|---|---|---|
| 28,722 | 6/1860 | Whitaker | 137/508 |
| 79,436 | 6/1868 | Bechtel | 137/508 |
| 1,139,455 | 5/1915 | Gase | |
| 1,159,214 | 11/1915 | Gueux | 137/508 |
| 1,199,152 | 9/1916 | Bruce | 137/508 |
| 2,207,382 | 7/1940 | McNamara | 137/508 |
| 2,290,151 | 7/1942 | McCollum | 137/508 |
| 2,879,783 | 11/1956 | Taplin | |
| 3,768,508 | 10/1973 | Schulte | |
| 3,769,982 | 11/1973 | Schulte | |
| 3,804,113 | 4/1974 | Garcea | |
| 3,827,439 | 8/1974 | Schulte et al. | |
| 3,889,687 | 6/1975 | Harris et al. | |
| 3,901,245 | 8/1975 | Spitz et al. | |
| 3,991,768 | 11/1976 | Portnoy | |
| 3,999,553 | 12/1976 | Spitz et al. | |
| 4,103,689 | 8/1978 | Leighton | |
| 4,156,422 | 5/1979 | Hildebrandt et al. | |
| 4,167,952 | 9/1979 | Reinicke | 137/508 |
| 4,332,255 | 6/1982 | Hakim et al. | |
| 4,437,493 | 3/1984 | Okuka et al. | |

Primary Examiner—C. Fred Rosenbaum
Assistant Examiner—Gene B. Kartchner
Attorney, Agent, or Firm—Lockwood, Alex, Fitzgibbon & Cummings

[57] ABSTRACT

An implantable valve for allowing the passage of cerebrospinal fluid (CSF) from a ventricle of the brain to a suitable drainage location in the body includes a movable diaphragm, one side of which is in pressure communication with the drainage location of the body and the other side of which is in pressure communication with the ventricular spaces of the brain. A valve assembly, actuable by displacement of the diaphragm in response to applied pressure differentials, regulates passage of CSF from the ventricular spaces to the drainage location. When the pressure differential is relatively small, the valve operates in a constant pressure mode to maintain a predetermined pressure differential across the valve. In response to a sudden increase in differential pressure, the valve mechanism operates in a constant flow mode to maintain a desired relatively constant CSF flow rate through the valve. Above a predetermined pressure differential, the valve operates in a constant pressure mode to maintain a predetermined maximum pressure differential across the valve. To simplify construction, the valve includes a single-piece valve stem having a ramp surface at one end and a fluid restrictor surface at the other end which cooperate with the valve diaphragm to provide the three operating modes.

15 Claims, 10 Drawing Figures

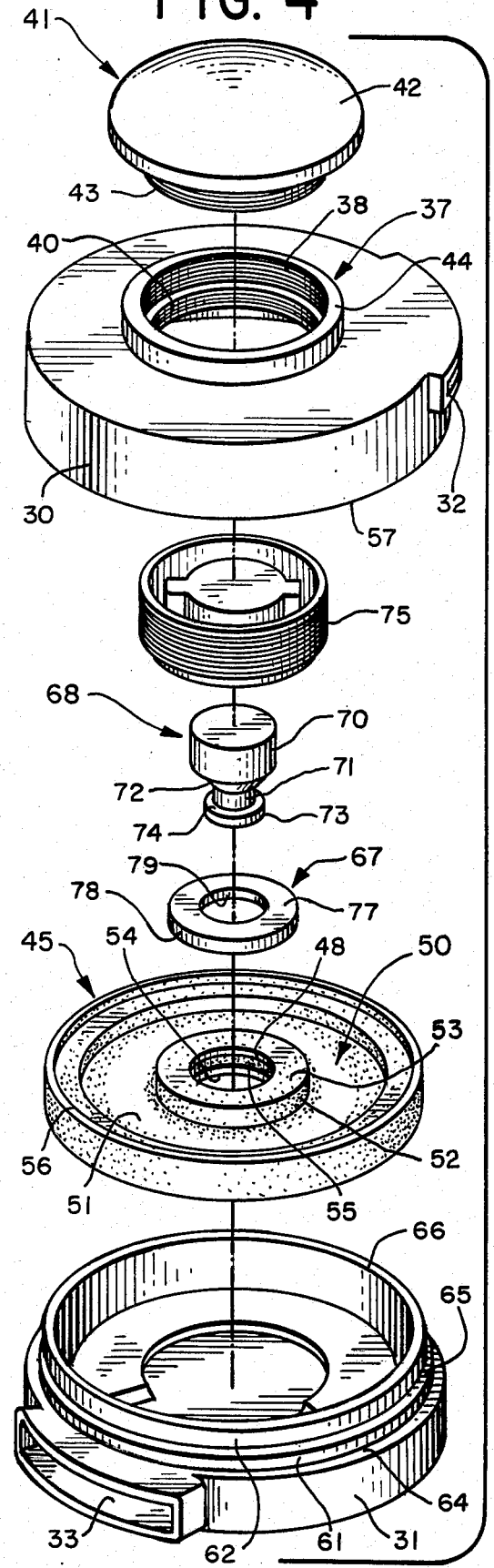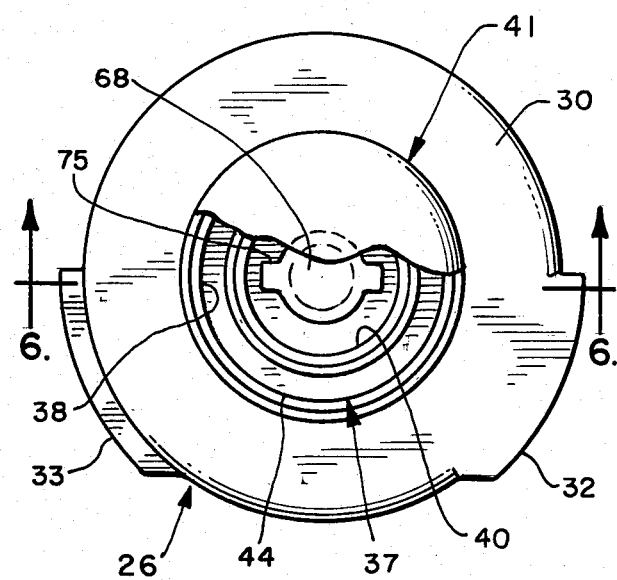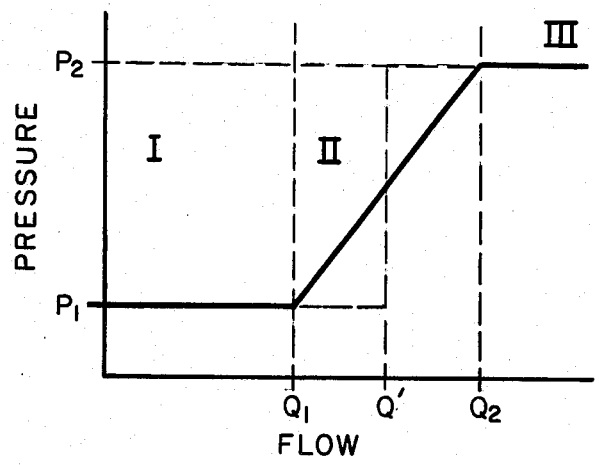

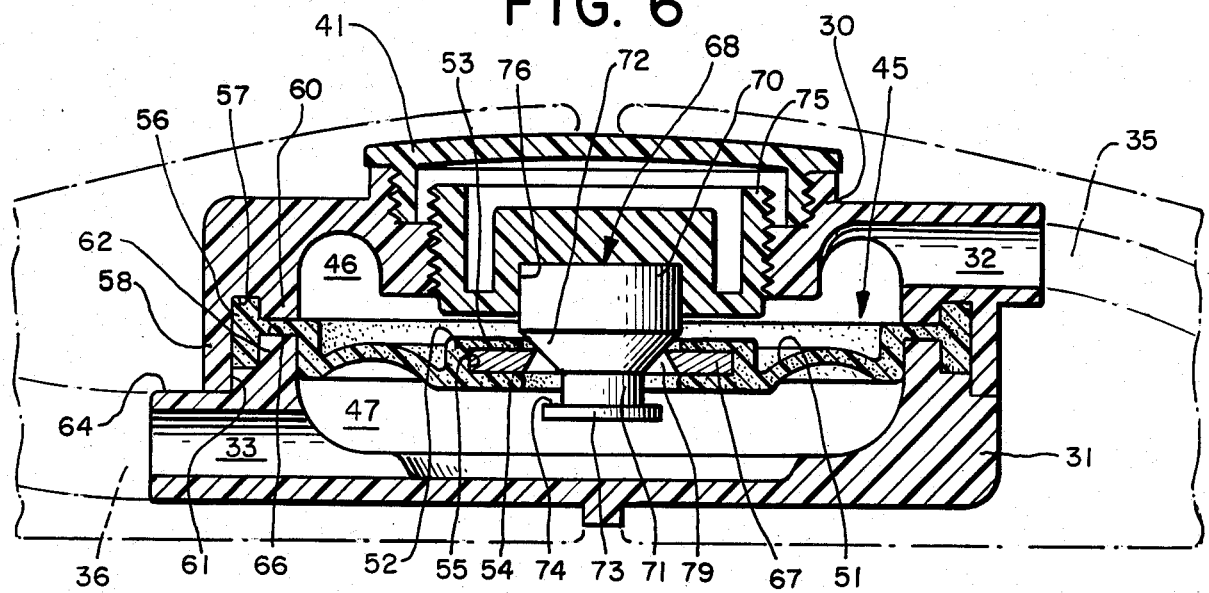
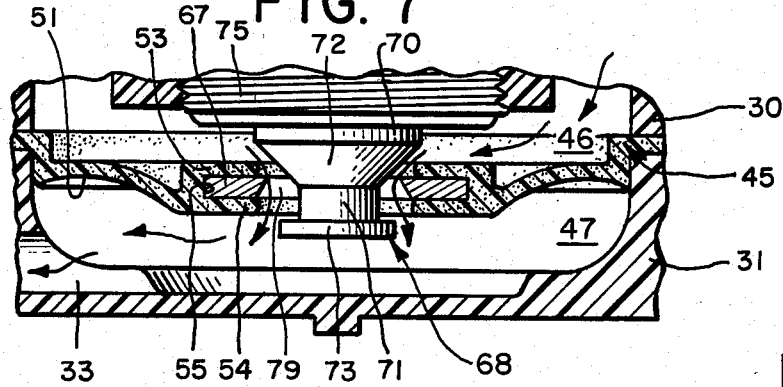
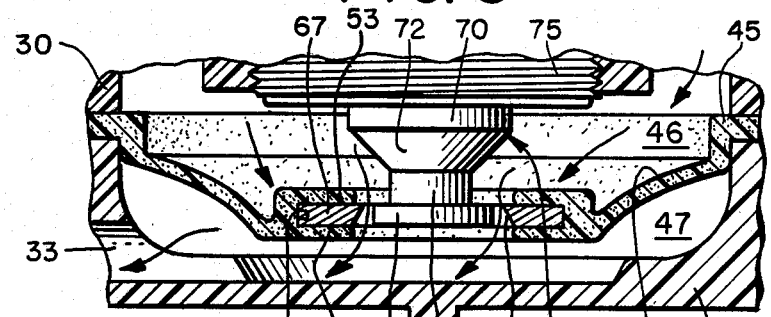
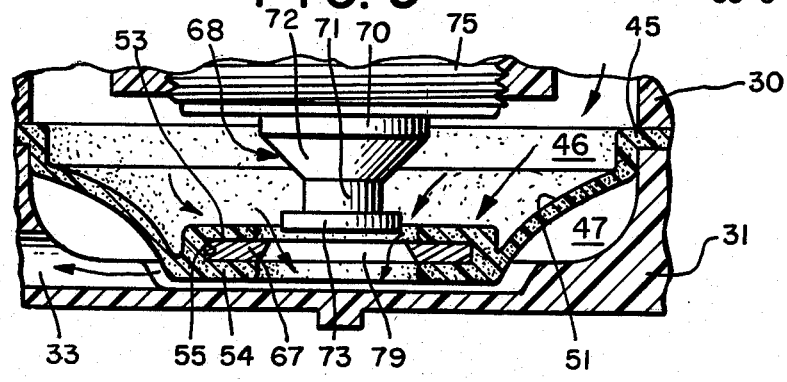

THREE STAGE INTRACRANIAL PRESSURE RELIEF VALVE HAVING SINGLE-PIECE VALVE STEM

BACKGROUND OF THE INVENTION

The present invention relates to an intracranial pressure relief valve and, more particularly, to a single piece combination valve stem and fluid flow restrictor for use in a three stage valve of the type which provides either constant pressure or constant flow characteristics in accordance with a fluid pressure differential applied across the valve.

Hydrocephalus is a condition in which the body, for any one of a variety of reasons, is unable to relieve itself of excess cerebrospinal fluid (CSF) collected in the ventricles of the brain. The excessive collection of CSF in the ventricles results in an abnormal increase in both epidural and intradural pressures. This in turn causes a number of adverse physiological effects including compression of brain tissue, impairment of blood flow in the brain tissue and impairment of the brain's normal metabolism.

Treatment of a hydrocephalic condition frequently involves relieving the abnormally high intracranial pressure. Accordingly, a variety of CSF pressure regulator valves and methods of controlling CSF pressur have been developed which include various check valves, servo valves or combinations thereof. Generally, such valves serve to divert CSF from the ventricles of the brain through a discharge line to some suitable drainage location in the body such as the venous system or the peritoneal cavity. Check valves operate by opening when the difference between CSF pressure and pressure in the discharge line exceeds a predetermined value.

The use of a simple check valve in the treatment of hydrocephalus is potentially disadvantageous since it is possible for such a valve to open in response to a sudden, but nevertheless perfectly normal, increase in differential pressure between CSF in the ventricular spaces and fluid at the selected discharge location of the body, resulting in abnormal and potentially dangerous hyperdrainage of the ventricular spaces. For example, when a patient stands after lying in a recumbent position, the resulting increased vertical height of the fluid column existing between the head and the selected drainage location may result in such an increase in differential pressure. Accordingly, valves, such as that described in the copending application of the present inventor, Ser. No. 559,392, filed Dec. 8, 1983, have been developed which serve to prevent undesired hyperdrainage by limiting the flow rate of fluid through the valve when a sudden increase in differential pressure occurs.

In this valve, a diaphragm, movable in response to the pressure differential between ventricular CSF pressure and pressure of fluids at the drainage location of the body, was mechanically coupled to a valve seat having a fluid metering orifice extending therethrough. The orifice allowed passage of CSF from the ventricular spaces to the selected drainage location. Motion of the diaphragm in response to changes in the differential pressure caused the valve seat to be moved from a first position, in which the valve seat contacted a suitably located sphere to block and thereby prevent the passage of fluid through the orifice, to a second position, in which a generally cylindrical fluid flow restrictor partially occluded the orifice, thereby limiting fluid flow therethrough. By controlling the position of the sphere, the valve seat and the restrictor, it was possible to construct a valve having flow characteristics which avoided hyperdrainage with sudden changes in differential pressure.

In order to assure optimum performance of such a valve, it was necessary to carefully control the dimensions of the sphere, the valve seat, the orifice and the restrictor. Since the parts involved were quite small, and involved working tolerances on the order of 0.0001 inch, considerable manufacturing costs were incurred in constructing such a valve.

The present invention is directed to an improvement in such a valve wherein the number of manufacturing steps, and hence the cost of the valve, is reduced. Basically, a valve constructed in accordance with the present invention is provided with a one-piece member which replaces both the sphere and the flow restrictor. Since the one-piece member does not include spherical surfaces, the difficulties associated with machining such a surface are avoided.

In view of the foregoing, it is a general object of the present invention to provide a new and improved pressure regulator valve for relieving intracranial pressure caused by the presence of excess CSF in the ventricles of the brain.

It is a more specific object of the present invention to provide a pressure regulator valve which includes components which may be easily and economically manufactured.

It is a still more specific object of the present invention to provide a pressure regulator valve in which critically dimensioned components are of an easily manufactured configuration.

SUMMARY OF THE INVENTION

The invention is directed to a valve for controlling the passage of body fluids from one location in the body to another location. The valve includes a housing having first and second interior chambers. An inlet port establishes fluid communication between the first chamber and the one location, while an outlet port establishes fluid communication between the second chamber and the other location. A valve mechanism, including a single-piece valve stem having a valve closure surface and a fluid flow restrictor portion integrally formed thereon, between the first chamber and the second chamber, is actuable to a first condition in which fluid communication between the first an second chambers is prevented. The valve mechanism is also actuable to a second condition in which fluid communication is provided between the first and second chambers at a flow rate sufficient to maintain a substantially constant desired first pressure in the first chamber, and to a third condition in which fluid communication is provided between the first and second chambers sufficient to maintain a desired substantially constant fluid flow rate. Finally, the valve mechanism is actuable to a fourth condition in which fluid communication is provided between the first and second chambers sufficient to maintain a substantially constant desired second pressure in the first chamber. The valve further includes a partition in the housing having a movable member which separates the first and second chambers and which is movable in response to the pressure differential therebetween. The movable member is operatively associated with the valve mechanism such that motion of the movable member in response to an increasing pressure differential between fluids in the first and second chambers sequentially conditions the valve mechanism from the first condition through the second and third conditions to the fourth condition whereby, in response to an increasing pressure differential between fluid at the one location and fluid at the other location, the valve sequentially prevents the passage of fluid between the one location and the other location, maintains a constant fluid pressure differential between the one location and the other location, maintains a desired constant rate of flow of fluid between the one location and the other location, and maintains a second constant desired fluid pressure differential between the one location and the other location.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 4 is an exploded perspective view of the pressure regulator valve showing the single-piece valve stem and other principal elements of the valve.

FIG. 5 is a top plan view, partially in section, of the three stage pressure regulator valve shown in FIG. 4.

FIG. 6 is an enlarged cross-sectional view of the pressure regulator valve taken along line 6—6 of FIG. 5.

FIG. 7 is a cross-sectional view, similar to FIG. 6, showing the pressure relief valve in a first constant pressure mode.

FIG. 8 is a cross-sectional view, similar to FIG. 6, showing the pressure relief valve in a constant flow-rate mode.

FIG. 9 is a cross-sectional view, similar to FIG. 6, showing the pressure relief valve in a second constant pressure mode.

FIG. 10 is a graphical depiction of certain pressure and flow characteristics of the three stage pressure relief valve useful in understanding the operation thereof.

DESCRIPTION OF THE PREFERRED EMBODIMENT

Figure 1:
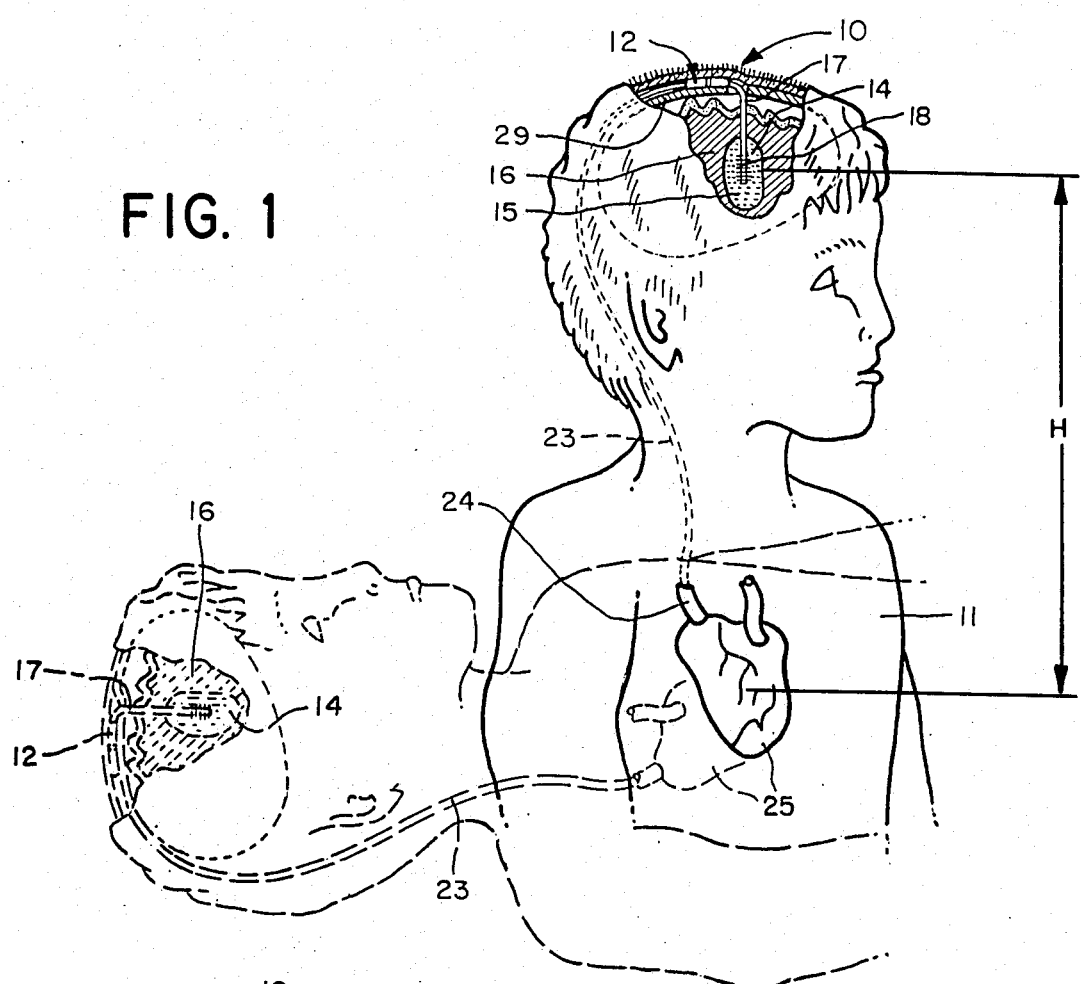
FIG. 1 is a perspective view, partially in section, of a CSF pressure relief system employing a three stage pressure regulator valve having a single piece valve stem constructed in accordance with the invention, showing such a system implanted within a patient.
Figure 2:
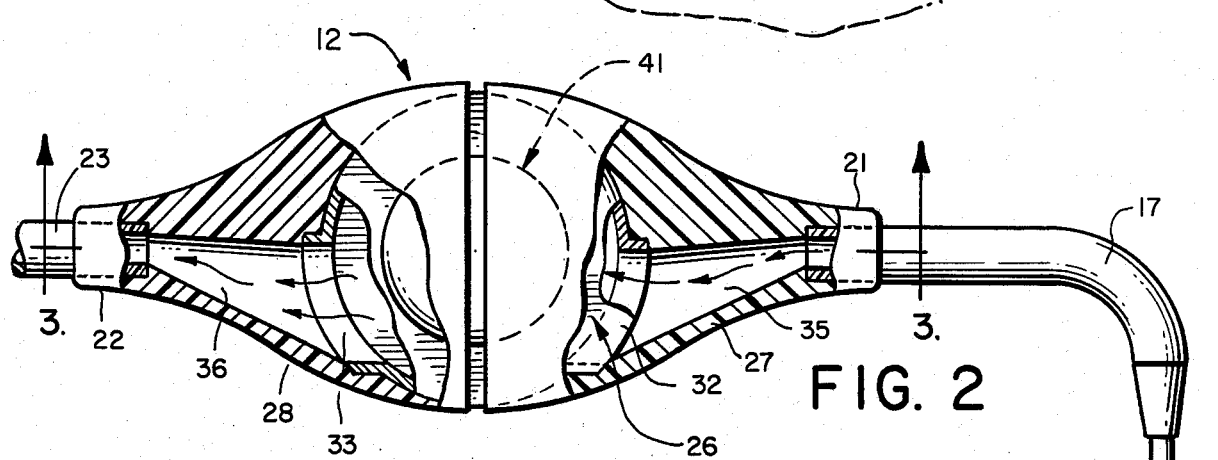
FIG. 2 is a plan view, partially in section, of the pressure regulator valve showing the principal elements thereof.
Figure 3:
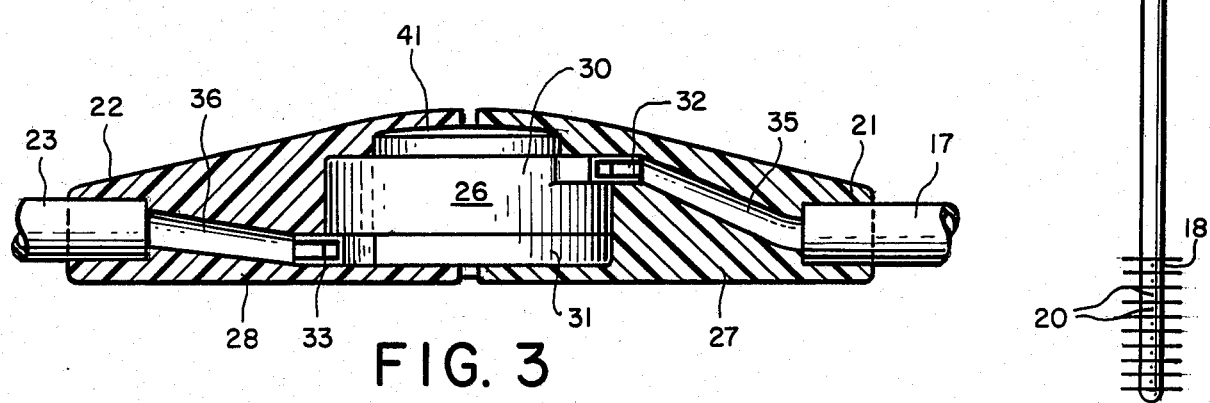
FIG. 3 is a cross sectional view of the pressure regulator valve taken along line 3—3 of FIG. 2.

Referring to the drawings, and particularly to FIGS. 1-3, a CSF pressure relief system 10 for maintaining a desired predetermined intracranial pressure in a patient 11 is illustrated. The system shown includes a three stage pressure relief valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement within the brain. The distal end 18 of the catheter may be provided with a plurality of apertures 20 (FIG. 2) for allowing the passage of CSF therethrough and is positioned in a suitable brain ventricle as illustrated. The other end of the catheter is coupled t the inlet port 21 of the valve to establish fluid communication between the valve and the ventricle. The outlet port 22 of the valve is attached to one end of a drain catheter 23, the opposite end of which discharges into an appropriate location in the patient's body. Although the drain catheter is shown threaded through an appropriate vein 24 to terminate within the right atrium of the heart 25, a different drainage location, such as, for example, the peritoneal cavity, could be selected instead. When open, pressure relief valve 12 allows passage of CSF from the brain ventricles to the selected discharge location to relieve excessive intracranial pressure caused by excessive accumulation of CSF. Typically, pressure relief valve 12 includes means for adjusting the differential pressure threshold at which it opens so that the hydrocephalus pressure relief system can be adjusted to suit the specific requirements of an individual patient.

While an increased differential pressure may result from the excessive accumulation of CSF in the brain ventricles, such an increase might also be a perfectly normal response to ordinary physical activity of the patient. For example, when a patient stands after lying for some time in a recumbent position, as illustrated in phantom in FIG. 1, the differential pressure will suddenly increase by reason of the sudden increase in vertical height H of the fluid column existing between the distal end of the ventricular catheter 17 and the drainage location. If the relief valve were to open and permit unrestrained fluid flow in response to this pressure increase, hyperdrainage of the ventricle, and a brain hematoma, are possible results. Accordingly, the valve includes means for preventing such unrestricted fluid flow to the drainage location in the event of a sudden increase in the differential pressure.

The internal construction and operation of the three stage valve may best be understood by reference to FIGS. 2-6. As illustrated, the valve includes a disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or a similar material bonded together over the inner housing. The dimensions of the inner and outer housings are selected so as to be compatible with subcutaneous implantation of the valve over the cranium 29 (FIG. 1).

As is best illustrated in FIGS. 3 and 4, the inner housing 26 comprises two circular cup-shaped housing members 30 and 31. Housing member 30 includes an inlet port 32, and housing member 31 includes an outlet port 33, by means of which fluid can pass to or from the interior region of the housing. In this regard, outer housing members 27 and 28 are provided with internal conduits 35 and 36, which provide fluid communication between inlet port 32, outlet port 33 and housing 26, respectively.

Upper housing member 30 is provided with an aperture 37 through the upper surface thereof. As illustrated in FIG. 4, the aperture 37 includes a region 38 of relatively larger diameter coaxially aligned above a region of relatively smaller diameter 40. Both the relatively larger diameter and smaller diameter regions of the aperture are internally threaded as illustrated. In order to seal the aperture while still allowing ready access to the interior region of the housing, the upper housing member 30 includes a removable cap 41 having a domed upper surface 42 and an externally threaded cylindrical lower portion 43 dimensioned to engage the threads of region 38 of aperture 37. To provide a tight seal between the cap and the housing, the upper housing member may include a raised annular seat 44 adjacent the periphery of the aperture against which the cap bears as it is turned into the upper housing member.

Referring to FIGS. 3, 4 and 6, pressure relief valve 12 includes partition means in the form of a diaphragm 45 which extends laterally across the interior region of the inner housing to divide that region into first and second interior chambers 46 and 47 (FIG. 6), respectively. The diaphragm 45 may be fashioned from a flexible biocompatible material, such as silicone rubber, and, as best seen in FIG. 4, may comprise a disc-shaped member having an aperture 48 provided centrally therethrough. The operative surface 50 of the diaphragm is provided with an annular groove 51 concentrically aligned with the center aperture which allows the operative surface to travel vertically in response to differential pressure across the diaphragm such as might result from a difference in pressures in the first and second interior chambers.

Toward its center, and in the region immediately surrounding the aperture, the thickness of the diaphragm 45 is increased to form a raised area 52, having upper and lower surfaces 53 and 54, respectively. An annular channel 55 of rectangular cross-section is provided in the sidewall of aperture 48 between surfaces 53 and 54. The diaphragm 45 also includes an integrally formed raised circular edge 56 projecting both above and below the operative surface 50 along its outer circumference. This edge facilitates installation of the diaphragm in the housing.

The manner in which the diaphragm is held in position relative to both the upper and lower housing member is best illustrated in FIGS. 4 and 6. The lower edge of the upper housing member is provided with a channel 57 thereby forming inner and outer sleeves 58 and 60 respectively. As illustrated, the vertical dimension of the inner sleev 58 is less than that of the outer sleeve 60 while channel 57 is dimensioned to receive the outer raised edge 56 of the diaphragm. The upper edge surface of the lower housing member is provided with a pair of raised steps 61 and 62 which form concentric annular ledges 64, 65 for receiving raised edge 56.

When assembled, the lower edge of the outer sleeve 58 contacts the first ledge 64, while the second ledge 65 is dimensioned so as to contact the lower edge 56 of the diaphragm when the diaphragm is in place. Similarly, the inner ledge 66 is dimensioned as to allow the diaphragm to be received in the space formed between the upper edge thereof and the lower edge of the interior sleeve 60.

When assembled, upper housing member 30 interlocks with lower housing member 31 by engagement of their corresponding edges. Diaphragm 45 is received in the space provided therebetween with its periphery fixed relative to the two interior housing members. When mounted in this manner, the operative surface 50 of the diaphragm is free to travel vertically in response to a pressure differential existing between fluids contained in the first and second chambers.

To regulate the passage of fluid from the first chamber 46 to the second chamber 47, and hence from a brain ventricle to the drainage area of the body, the valve includes valving means for regulating fluid communication between the first and second chambers. These valving means, in accordance with the invention, take the form of a valve seat 67 mounted for movement with diaphragm 45, and valve closure means and fluid restrictor means contained on a generally cylindrical single-piece valve stem 68.

Referring to FIGS. 4 and 6, the single-piece valve stem 68 includes a generally cylindrical upper region 70 of relatively larger diameter above a generally cylindrical region of relatively smaller diameter 71. The diameter of the valve stem uniformly increases between the smaller and larger diameter regions to form a frustoconical ramped surface 72 therebetween. A third generally cylindrical region 73 of intermediate diameter is provided at the lowermost end of smaller diameter region 71 to form a fluid flow restrictor. Restrictor 73 defines an annular ledge 74 where it joins the smaller diameter region 71.

The single-piece valve stem 68 is positioned above and in coaxial alignment with valve seat 67 and is held in position by means of a cylindrical collar 75 externally threaded and dimensioned to engage the threads of the relatively smaller diameter segment 40 of aperture 37. Collar 75 includes a central recess 76 dimensioned to receive the relatively larger diameter region 70 of valve stem 68 and can be engagingly or disengagingly rotated relative to upper housing member 30 whereby the vertical position of the stem relative to diaphragm 45 can be adjusted.

The valve seat 67, which may be formed of the same material as the single piece valve stem 68, comprises a disc-shaped member having flat, parallel, upper and lower faces 77 and 78 (FIG. 4). The valve seat is received within the channel 55 formed in the raised segment 52 of diaphragm 45. The valve seat 67 includes a generally circular orifice 79 extending centrally therethrough which provides fluid communication between the first and second chambers 46 and 47. The diameter of the orifice is greater than that of the smaller diameter region 71 of the valve stem, but less than that of the larger diameter region 70. As illustrated, the valve seat is located directly beneath the valve stem so that the stem projects through the orifice.

When no differential pressure acts on diaphragm 45, valve seat 67 contacts ramp surface 72 and orifice 79 is totally occluded to prevent the passage of CSF between the first and second chambers. Downward travel of the diaphragm and the valve seat progressively opens the orifice, eventually resulting in the introduction of restrictor 73 and the partial occlusion of the passage between the first and second chambers.

It will be observed that the orifice 79 is not a simple cylindrical aperture but rather is tapered so that the orifice is narrowest at the upper surface 77 and widest at the lower surface 78 of the valve seat. The dimension of the restrictor 73 is selected so that it will barely pass through the orifice at its narrowest point. By way of example, in one embodiment of the valve, the valve seat orifice had a diameter of 0.040 inches at its narrowest point and the clearance between the restrictor and the orifice at the narrowest point was on the order of 0.001 inches.

The operation of the valve is illustrated in FIGS. 6-10. FIG. 6 illustrates the operation of the valve in the absence of applied CSF pressures. FIGS. 7-9 illustrate the operation of the valve in response to various levels of CSF pressures. FIG. 10 is a graphical depiction of pressure versu flow characteristics of the valve.

Basically, the pressure relief valve 12 normally operates to maintain a predetermined differential pressure $P_1$ between fluids in the brain ventricles and at the selected discharge location of the body. The valve accomplishes this by adjusting the fluid flow rate Q so that the pressure $P_1$ is maintained. This operation of the valve is shown in region I of FIG. 10.

When differential pressure rapidly increases, such as when the patient stands, a flow rate greater than a preselected rate $Q_1$ is necessary to maintain pressure $P_1$. However, such a flow rate may create the risk of undesirable hyperdrainage of the brain ventricles. Accordingly, when a rapid increase in differential pressure occurs, the valve automatically serves to maintain a relatively constant desired rate of fluid flow despite changes in differential pressure, as depicted in region II of FIG. 10. In a practical valve, the flow rate will not be entirely independent of the applied differential pressure but rather will increase from a lower flow rate $Q_1$ to a higher flow rate $Q_2$ as differential pressure increases between first pressure $P_1$ and a second pressure $P_2$, as indicated by the solid line in FIG. 10. Flow rates $Q_1$ and $Q_2$ are sufficiently low so that during a temporary rapid increase in differential pressure, pressure will return to normal before a quantity of CSF sufficient to cause adverse side effects may flow through the valve. In a typical valve $Q_1$ and $Q_2$ might be 0.4 ml./min and 0.8 ml./min., respectively, while first and second pressures, $P_1$ and $P_2$, may have values of 80 and 350 millimeters of water, respectively.

While it is desirable to avoid high flow rates through the valve in order to avoid hyperdrainage of the ventricles, it may, under certain emergency conditions, be desirable to allow rapid shunting of CSF in order to avoid possible brain damage. When the valve is operating in region II, increases in differential pressure tend to close the valve between the first and second interior chambers. To avoid the possibility of building extremely high ventricular CSF pressure, the valve is constructed so that when differential pressure exceeds a predetermined pressure $P_2$ substantially higher than pressure $P_1$, the valve once again operates to allow a fluid flow rate sufficient to maintain a differential pressure no higher than pressure $P_2$. This operation is depicted in region III of FIG. 10. When the valve is operating in this region, further increases in differential presisure result in an increase in fluid flow through the valve thereby stabilizing differential pressure.

FIGS. 6-9 illustrate operation of the valve in the regions previously described. CSF applied to the inlet port 21 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts a upwardly directed force on the lower surface of the diaphragm. Accordingly, the differential pressure between CSF in the brain ventricle and fluid at the drainage location results in vertical deflection of both the diaphragm and the valve seat 67 rigidly attached thereto.

As shown in FIG. 6, when differential pressure is negative or non-existent, valve seat 67 contacts ramped surface 72 and the orifice 79 is totally occluded, thereby preventing CSF flow between chambers 46 and 47.

When the differential pressure is relatively low, such as when the valve is operating in region I of FIG. 10, the resulting slight downward displacement of the diaphragm is sufficient to displace the valve seat 67 relative to the valve stem 68 as shown in FIG. 7, thereby allowing CSF to pass through orifice 79 from chamber 46 to chamber 47. As shown, the downward deflection of the diaphragm is sufficient to allow the passage of CSF through the orifice, yet the upper surface of the restrictor 70 is sufficiently removed from the orifice so as not to interfere with the flow of CSF between the chambers. Thus, the valve acts primarily as a constant pressure device whereby the pressure differential $P_1$ is maintained between the CSF in chambers 46 and 47. An increase in differential pressure results in a downward deflection of the diaphragm, thereby further opening the valve to allow greater CSF flow between the chambers. Similarly, a decrease in pressure allows the diaphragm to move toward the valve seat, restricting flow between the chambers and causing pressure in chamber 46 to increase. It will be noted that the regulated pressure level $P_1$ in this mode can be adjusted by rotating collar 75 to vary the vertical position of the valve stem relative to the valve seat.

FIG. 8 illustrates the operation of the valve when a sudden increase in differential pressure is applied to the valve. When such an event occurs, the pressure differential exceeds the predetermined regulated pressure $P_1$ and the valve operates in region II of FIG. 10. The downward displacement of the diaphragm 45 is now sufficient to cause valve seat 67 to descend over the restrictor 73, causing the restrictor to partially occlude orifice 79. Because the orifice is tapered, additional downward travel of the valve seat results in a further occlusion of the orifice. The orifice is shaped such that the additional occlusion occuring by reason of increasing differential pressure is sufficient to offset the higher flow rate ordinarily resulting from increased pressure, resulting in a relatively uniform rate fluid flow between the chambers despite an increase in differential pressure. Accordingly, in this condition, the valve acts primarily as a constant flow device permitting the passage of fluid from chamber 46 to chamber 47 at a relatively constant predetermined rate despite changes in applied differential pressure.

FIG. 9 illustrates operation of the valve in region III of FIG. 10, such as would occur when the differential pressure exceeds a predetermined pressure level $P_2$. In this condition, differential pressure displaces the diaphragm to a degree sufficient to cause the restrictor 73 to extend past the upper surface of valve seat 67 so as to allow CSF to flow past the restrictor and through orifice 79. The orifice is now less restricted than in Region II, wherein the restrictor 73 is received within the tapered region of valve seat 67. When the valve is operating in this manner, increases in differential pressure cause the valve seat to be further displaced away from the restrictor, thereby further opening the orifice, and allowing a greater fluid flow rate. Thus, the valve operates essentially as a constant pressure device whereby differential pressure greater than the predetermined maximum pressure $P_2$ is prevented.

A further advantage of this construction is that as restrictor 73 passes through orifice 79 it tends to remove foreign materials which may tend to clog the valve. Should clogging occur, the resulting increased differential pressure eventually causes the restrictor to pass through the orifice to provide the valve with a self-cleaning feature.

The valve stem 68, which may be advantageously formed as a single-piece member from a hard bio-compatible material such as ruby, sapphire or the like, includes only surfaces which can be accurately formed by economical well known lathe machining operations. By reason of the threaded valve stem carrier 75, the valve stem can be accurately positioned relative to valve member 67 and the other valve elements for optimum performance in a wide range of applications.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A valve for regulating the flow of fluid from one location in the body to another location, comprising:
    a bio-compatible housing;
    a flexible bio-compatible diaphragm dividing the interior of said housing into first and second interior chambers;
    inlet port means for establishing fluid communication between said first interior chamber and the one location;
    outlet port means for establishing fluid communication between said second interior chamber and the other location;
    a bio-compatible valve seat carried on said diaphragm for movement therewith, said valve seat defining a fluid passageway having a predetermined minimum diameter and opening from said first interior chamber to said second interior chamber, and defining a first valving surface concentrically oriented with respect to the axis of said fluid passageway, said valve seat and diaphragm having a static position within said housing in the absence of a pressure differential between said chambers;
    means comprising an elongated bio-compatible valve closure member attached at one end to said housing within said first interior chamber and extending therefrom through said fluid passageway into said second interior chamber, said valve closure member being axially aligned with the axis of said passageway and defining a second valving surface concentrically oriented with respect to said axis for coacting with said first valving surface to form a flow restriction within said passageway between said first and second chambers;
    said second valving surface including, progressing from said valve closure member, a first portion progressively decreasing in diameter from a first predetermined diameter greater than said minimum diameter of said passageway to a second predetermined diameter less than said minimum diameter, and a second portion of finite axial extend having a maximum diameter greater than said second predetermined diameter and less than said mimimum diameter of said passageway;
    said second valving surface coacting with said first portion of said first valving surface when said valve seat is in said static position to close said passageway to provide a first valving mode wherein said flow between said first and second interior chambers is prevented; and
    said diaphragm being displaceable from said static position in a direction along said axis of said fluid passageway away from said one end of said valve closure member in response to an increase in pressure differential between said first interior chamber and said second interior chamber to cause said first valving member to successively coact with said first and second portions of said second valving surface, and successively to be axially spaced from said second portion, thereby providing second, third and fourth valving modes, in said second valving mode fluid flow occurring between said interior chambers so as to maintain a first substantially constant predetermined pressure in said first chamber, in said third valving mode fluid flow remaining substantially constant between said chambers notwithstanding changes in differential pressure, and in said fourth valving mode fluid flow occurring between said chambers to maintain a second substantially constant predetermined pressure in said first interior chamber.

2. A flow regulating valve as defined in claim 1 wherein said first valving surface is biased into engagement with said second valving surface by said diaphragm when said valve seat is in said static position to provide a predetermined threshold pressure differential at which flow occurs between said first and second interior chambers.

3. A flow regulating valve as defined in claim 1 wherein said second valving surface of said valve closure member includes an intermediate portion of substantially constant diameter and of finite axial extent intermediate said first and second portions.

4. A flow regulating valve as defined in claim 1 wherein said valve seat defines a frusto-conical valving surface of progressively increasing diameter along the axis of said passageway.

5. A flow regulating valve as defined in claim 1 wherein said second portion of said second valving surface is of substantially constant diameter.

6. A flow regulating valve as defined in claim 5 wherein said valve seat defines a frusto-conical valving surface of progressively increasing diameter along the axis of said passageway.

7. A flow regulating valve as defined in claim 1 wherein said valve closure member is of integral one-piece construction.

8. A flow regulating valve as defined in claim 1 wherein said valve closure member is adjustably mounted to said housing for movement along the axis of said passageway.

9. A flow regulating valve as defined in claim 8 wherein said valve closure member is threadably mounted to said housing.

10. A valve for regulating the flow of fluid from one location in the body to another location, comprising:
    a bio-compatible housing;
    a flexible bio-compatible diaphragm dividing the interior of said housing into first and second interior chambers;

inlet port means for establishing fluid communication between said first interior chamber and the one location;

outlet port means for establishing fluid communication between said second interior chamber and the other location;

a bio-compatible valve seat carried on said diaphragm for movement therewith, said valve seat defining a fluid passageway having a predetermined minimum diameter and opening from said first interior chamber to said second interior chamber, and defining a first valving surface concentrically oriented with respect to the axis of said fluid passageway, said valve seat and diaphragm having a static position within said housing in the absence of a pressure differential between said chambers;

means comprising an elongated bio-compatible valve closure member attached at one end to said housing within said first interior chamber and extending therefrom through said fluid passageway into said second interior chamber, said valve closure member being axially aligned with the axis of said passageway and defining a second valving surface concentrically oriented with respect to said axis for coacting with said first valving surface to form a flow restriction within said passageway between said first and second chambers;

said second valving surface including, progressing from said one end of said valve closure member, a first portion porgressively decreasing in diameter from a first predetmined diameter greater than said minimum diameter of said passageway to a second predetermined diameter less than said minimum diameter, a second portion of finite axial extend having a maximum diameter greater than said second predetermined diameter and less than said minimum diameter of said passageway, and an intermediate portion having said second predetermined diameter and of finite axial extent intermediate said first and second portions;

said second valving surface coacting with said first portion of said first valving surface when said valve seat is in said static position to close said passageway to provide a first valving mode wherein said flow between said first and second interior chambers is prevented; and said diaphragm being displaceable from said static position in a direction along said axis of said fluid passageway away from said one end of said valve closure member in response to an increase in pressure differential between said first interior chamber and said second interior chamber to cause said first valving member to successively coact with said first and second portions of said second valving surface, and successively to be axially spaced from said second portion, thereby providing second, third and fourth valving modes, in said second valving mode fluid flow occurring between said interior chambers so as to maintain a first substantially constant predetermined pressure in said first chamber, in said third valving mode fluid flow remaining substantially constant between said chambers notwithstanding changes in differential pressure, and in said fourth valving mode fluid flow occurring between said chambers to maintain a second substantially constant predetermined pressure in said first interior chamber.

11. A flow regulating valve as defined in claim 10 wherein said valve seat defines a frusto-conical valving surface of progressively increasing diameter along the axis of said passageway.

12. A flow regulating valve as defined in claim 10 wherein said valve closure member is of integral one-piece construction.

13. A flow regulating valve as defined in claim 10 wherein said valve closure member is adjustably mounted to said housing for movement along the axis of said passageway.

14. A flow regulating valve as defined in claim 8 wherein said valve closure member is threadably mounted to said housing.

15. A valve for regulating the flow of CSF from one location in the body of another location, comprising:
a bio-compatible housing;
a flexible bio-compatible diaphragm dividing the interior of said housing into first and second interior chambers;
inlet port means for establishing fluid communication between said first interior chamber and the one location;
outlet port means for establishing fluid communication between said second interior chamber and the other location;
a bio-compatible valve seat carried on said diaphragm for movement therewith, said valve seat defining a fluid passageway having a predetermined minimum diameter and opening from said first interior chamber to said second interior chamber, and defining a frusto-conical first valving surface, concentrically oriented and of progressively increasing diameter along the axis of said fluid passageway, said valve seat and diaphragm having a static position within said housing in the absence of a pressure differential between said chambers;
means comprising an elongated one-piece bio-compatible valve closure member threadably mounted at one end to said housing within said first interior chamber, and extending therefrom through said fluid passageway into said second interior chamber, said valve member being axially aligned with and adjustably movable along the axis of said passageway and defining a second valving surface concentrically oriented with respect to said axis for coacting with said first valving surface to form a flow restriction within said passageway between said first and second chambers;
said second valving surface including, progressing from one end of said valve closure member, a first portion progressively decreasing in diameter from a first predetermined diameter greater than said minimum diameter of said passageway to a second predetermined diameter less than said minimum diameter, a second portion of finite axial extent having a maximum diameter greater than said second predetermined diameter and less than said minimum diameter of said passageway, and an intermediate portion having a diameter equal to said second predetermined diameter and of finite axial extent intermediate said first and second portions;
said second valving surface being biased into engagement with said first portion of said first valving surface by said diaphragm when said valve seat is in said static position to close said passageway and provide a first valving mode wherein flow between said first and second interior chambers occurs only when the pressure differential between said chambers exceeds a predeterminded threshold level; and said diaphragm being displaceable from said static position in a direction along said axis of said fluid passageway away from said one end of said valve closure member in response to an increase in pressure differential between said first interior chamber and said second interior chamber to cause said first valving member to successively coact with said first, intermediate and second portions of said second valving surface, and successively to be axially spaced from said second portion, thereby providing second, third and fourth valving modes, in said second valving mode fluid flow occurring between said interior chambers so as to maintain a first substantially constant predetermined pressure in said first chamber, in said third valving mode fluid flow remaining substantially constant between said chambers notwithstanding changes in differential pressure, and in said fourth valving mode fluid flow occurring between said chambers to maintain a second substantially constant predetermined pressure in said first chamber.

* * * * *